United States Patent
Majeed et al.

(10) Patent No.: US 11,707,438 B2
(45) Date of Patent: Jul. 25, 2023

(54) CURCUMINOID COMPOSITION FOR THERAPEUTIC MANAGEMENT OF METABOLIC SYNDROME

(71) Applicants: Muhammed Majeed, Bangalore (IN); Kalyanam Nagabhushanam, East Windsor, NJ (US); Lakshmi Mundkur, Bangalore (IN); Rajendran Ramanujam, Bangalore (IN)

(72) Inventors: Muhammed Majeed, Bangalore (IN); Kalyanam Nagabhushanam, East Windsor, NJ (US); Lakshmi Mundkur, Bangalore (IN); Rajendran Ramanujam, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 123 days.

(21) Appl. No.: 17/071,637

(22) Filed: Oct. 15, 2020

(65) Prior Publication Data

US 2021/0106543 A1   Apr. 15, 2021

Related U.S. Application Data

(60) Provisional application No. 62/915,068, filed on Oct. 15, 2019.

(51) Int. Cl.
| | | |
|---|---|---|
| *A61K 31/12* | (2006.01) | |
| *A61P 1/16* | (2006.01) | |
| *A61P 31/14* | (2006.01) | |
| *A61P 11/00* | (2006.01) | |
| *A61P 29/00* | (2006.01) | |

(52) U.S. Cl.
CPC .............. *A61K 31/12* (2013.01); *A61P 1/16* (2018.01); *A61P 11/00* (2018.01); *A61P 29/00* (2018.01); *A61P 31/14* (2018.01)

(58) Field of Classification Search
CPC ... A61K 31/12; A61P 1/16; A61P 3/00; A61P 3/06; A61P 3/10
See application file for complete search history.

(56) References Cited

U.S. PATENT DOCUMENTS

2017/0258743 A1*  9/2017  Gopi .................. C08B 37/0015

OTHER PUBLICATIONS

Hewlings et al; "Curcumin: A review of its effects on human health," Foods, 2017, 6. 92. (Year: 2017).*
Pan et al. "Attenuation by tetrahydrocurcumin of adiposity and hepatic steatosis in mice with high-fat-diet-induced obesity," Agricultural and Food Chemistry, 2018, vol. 66, pp. 12685-12695 (Year: 2018).*

* cited by examiner

*Primary Examiner* — Shengjun Wang

(57) ABSTRACT

The present invention discloses a composition comprising 70%-80% w/w tetrahydrocurcuminoids, 10%-20% w/w hexahydrocurcuminoids and 5%-10% w/w octahydrocurcuminoids and its therapeutic application. More specifically, the present invention discloses the use of a composition comprising 70%-80% w/w tetrahydrocurcuminoids, 10%-20% w/w hexahydrocurcuminoids and 5%-10% w/w octahydrocurcuminoids in the therapeutic management of metabolic syndrome in mammals.

30 Claims, 3 Drawing Sheets
(1 of 3 Drawing Sheet(s) Filed in Color)

CURCUMINOID COMPOSITION FOR THERAPEUTIC MANAGEMENT OF METABOLIC SYNDROME

CROSS-REFERENCE TO RELEGATED APPLICATION

This is a non-provisional filing claiming priority from US provisional application No. 62/915,068, filed on 15 Oct. 2019, the subject matter of which is incorporated herein by reference.

FILED OF INVENTION

The present invention relates to a curcuminoid composition and its therapeutic applications thereof. More specifically the invention relates to the composition comprising Tetrahydrocurcuminoids (THC), Hexahydrocurcuminoids (HHC) and Octahydrocurcuminoids (OHC) and their potential in alleviating symptoms of metabolic syndrome.

BACKGROUND OF THE INVENTION

Description of Prior Art

Metabolic syndrome is a cluster or combination of metabolic disorders that increase a person's risk for heart disease, diabetes, and stroke. The term metabolic refers to the biochemical processes occurring in the body. According to National Institutes of Health (NIH), it is a serious global health challenge with 23% of adult population exposed to increased risk of cardiovascular disease, diabetes, and stroke. A person will be at increased risk for cardiovascular problems if he/she presents with these conditions together than any one factor presenting alone (Metabolic Syndrome, National Heart, Lung and Blood institute, U.S. Dept of Health and Human Services, nhlbi.nih.gov/health-topics/metabolic-syndrome). Of the risk factors involved in the development of metabolic syndrome, obesity is considered to be the main causative factor. It is responsible for the development of chronic conditions ranging from cardiovascular diseases, hypertension, type II diabetes, metabolic syndrome, and stroke to osteoarthritis and cancer. The following prior art documents reviews the different pathological features responsible for the development of metabolic syndrome:

i) Marjani A, A Review on Metabolic Syndrome, Journal of Endocrinology and Metabolism, 2012; 2(4-5): 166-170.
ii) Schindler C, The metabolic syndrome as an endocrine disease: is there an effective pharmacotherapeutic strategy optimally targeting the pathogenesis? Ther Adv Cardiovasc Dis, 2007; 1(1):7-26.
iii) Srikanthan et al., Systematic Review of Metabolic Syndrome Biomarkers: A Panel for Early Detection, Management, and Risk Stratification in the West Virginian Population, Int J Med Sci 2016; 13(1):25-38.
iv) Rochlani et al., Metabolic syndrome: pathophysiology, management, and modulation by natural compounds, Ther Adv Cardiovasc Dis 2017; 11(8):215-225.

Lifestyle modifications, including diet and exercise interventions are the recommended treatment modalities for managing metabolic syndrome (Castro-Barquero et al., Dietary Strategies for Metabolic Syndrome: A Review, J Obes Ther 1:2; Al-Qawasmeh et al., Dietary and Lifestyle Risk Factors and Metabolic Syndrome: Literature Review, Curr Res Nutr Food Sci 2018; 6(3)). However, pharmacotherapy may be considered if the interventions are ineffective for obese individuals with a BMI≥30 or for those with a BMI≥27 when co-morbidities, such as hypertension or type II diabetes are diagnosed. The drugs that are typically used in the treatment of metabolic syndrome are disclosed by Marvasti et al., Pharmacological management of metabolic syndrome and its lipid complications; Dam. 2010; 18(3): 146-154. However, drugs that can effectively reduce all of the metabolic risk factors are prone to cause undesirable side effects (Anti-Obesity Drugs: A Review about Their Effects and Safety, Jun Goo Kangl and Cheol-Young Park, Diabetes Metab J. 2012 February; 36(1): 13-25; Drug therapy of the metabolic syndrome: minimizing the emerging crisis in polypharmacy, Grundy S M, Nat Rev Drug Discov. 2006 April; 5(4):295-309). A therapeutic alternative which is natural, safe, efficacious, and sustainable in managing the metabolic syndrome is warranted.

Natural compounds are now being evaluated for managing metabolic syndrome (Rochlani et al., Metabolic syndrome: pathophysiology, management, and modulation by natural compounds, Ther Adv Cardiovasc Dis 2017; 11(8): 215-225). Curcumin, isolated from *Curcuma* sp. has been reported to be very effective is reducing the symptoms of metabolic syndrome. Recently metabolites of curcuminoids are garnering the much attention owing to their similar and superior efficacy over curcumin (Majeed et al., Reductive Metabolites of Curcuminoids, Nutriscience Publishers LLC, 2019). The pharmacological activities of reductive metabolites of curcumin such as tetrahydrocurcumin, as represented by STR#1, hexahydrocurcumin as represented by STR#2 and octahydrocurcumin as represented by STR#3 are yet to be proven and tapped for industrial application. The reductive metabolites also include tetrahydro-demethoxycurcumin (STR#4), tetrahydrobis-demethoxycurcumin (STR#5), hexahydro-demethoxycurcumin (STR#6), hexahydrobis-demethoxycurcumin (STR#7), octahydro-demethoxycurcumin (STR#8) and octahydrobis-demethoxycurcumin (STR#9).

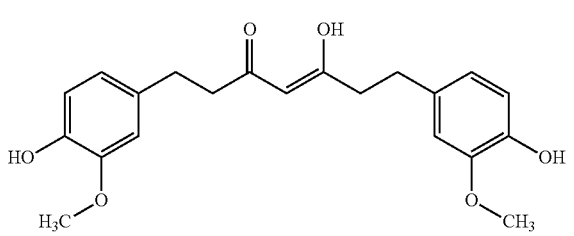

STR#1

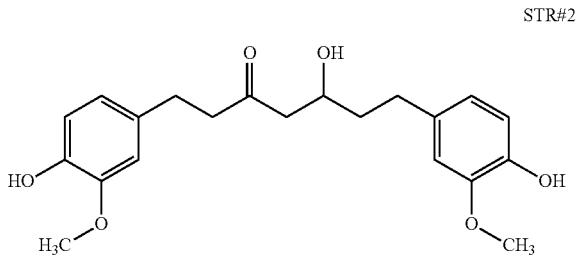

STR#2

-continued

STR#3
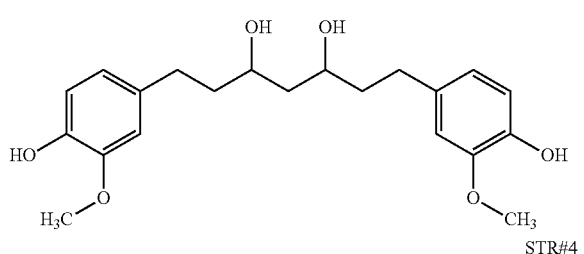

STR#4
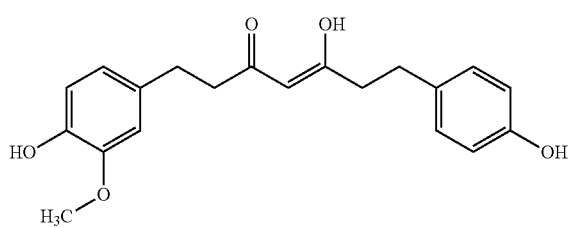

STR#5
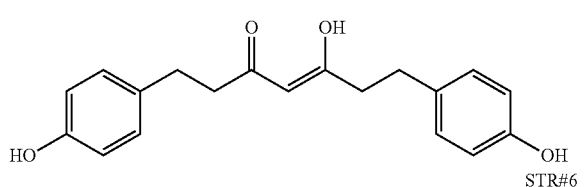

STR#6
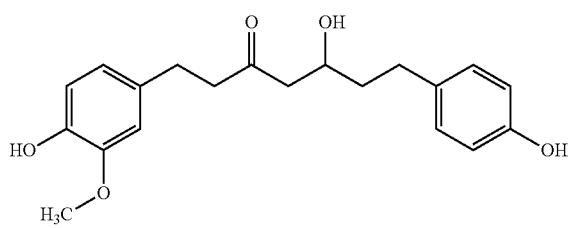

STR#7
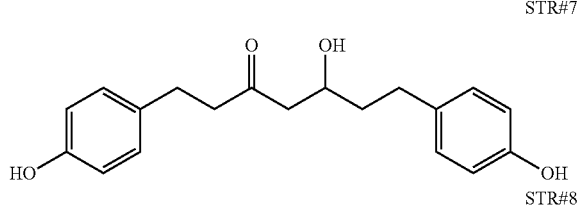

STR#8
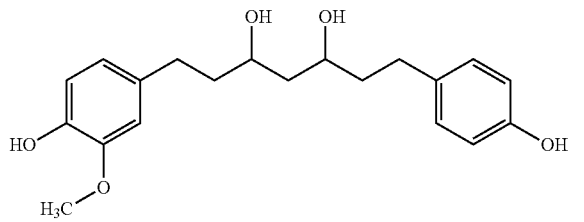

STR#9
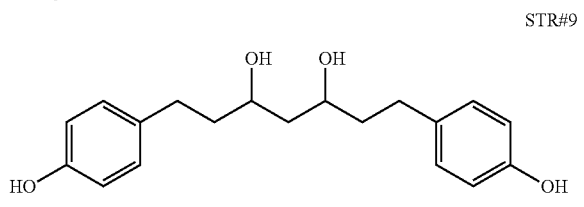

These reductive metabolites of curcumin are commonly biotransformed by the reductive enzymes (Mimura et. al., U.S. Pat. No. 5,266,344; Pan et al., Biotransformation of curcumin through reduction and glucuronidation in mice, Drug Metab Dispos, 1999, 27(1):486-494). They are also identified in nature and isolated from different plant sources (Majeed et al., Reductive Metabolites of Curcuminoids, Nutriscience Publishers LLC. 2019). The present invention discloses a composition comprising metabolites of curcuminoids, specifically tetrahydrocurcumin, hexahydrocurcumin and octahydrocurcumin and its therapeutic potential in the management of metabolic syndrome.

It is the principle object of the invention to disclose a composition comprising tetrahydrocurcumin, hexahydrocurcumin and octahydrocurcumin for use in the management of metabolic syndrome.

It is another object of the invention to disclose the use of a composition comprising tetrahydrocurcumin, hexahydrocurcumin and octahydrocurcumin in the therapeutic management of dyslipidemia.

It is another object of the invention to disclose the use of a composition comprising tetrahydrocurcumin, hexahydrocurcumin and octahydrocurcumin in the therapeutic management of liver dysfunction.

It is another object of the invention to disclose the use of a composition comprising tetrahydrocurcumin, hexahydrocurcumin and octahydrocurcumin in the therapeutic management of diabetes and associated hyperglycemia.

It is another object of the invention to disclose the use of a composition comprising tetrahydrocurcumin, hexahydrocurcumin and octahydrocurcumin in inhibiting adipogenesis.

The present invention fulfils the abovementioned objects and provides further related advantages.

SUMMARY OF THE INVENTION

In a most preferred embodiment, the invention discloses a method for the therapeutic management of metabolic syndrome in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management.

In another preferred embodiment, the invention discloses the use of a composition comprising 70%-80% w/w tetrahydrocurcuminoids, 10%-20% w/w hexahydrocurcuminoids and 5%-10% w/w octahydrocurcuminoids in the therapeutic management of metabolic syndrome in mammals.

In another most preferred embodiment, the invention discloses a method for the therapeutic management of hyperlipidemia in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management to bring about an effect of reducing the levels of a) total cholesterol, b) LDL and c) triglycerides and increasing the levels of HDL in said mammals.

In yet another preferred embodiment, the invention discloses a method for the therapeutic management of diabetes and associated hyperglycemia in mammals, said method comprising step of administering an effective dose, based on the body weight of said mammal, a composition comprising 70%-80% w/w tetrahydrocurcuminoids, 10%-20% hexahydrocurcuminoids and 5%-10% octahydrocurcuminoids to mammals in need of such therapeutic management.

In another embodiment, the invention discloses a method for the therapeutic management of liver dysfunction in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management to reduce the elevated levels of liver enzymes.

In another preferred embodiment, the invention discloses a method for inhibiting adipogenesis in mammalian cells, said method comprising step bringing into contact, mammalian adipocytes with a composition comprising 70%-80% w/w tetrahydrocurcuminoids, 10%-20% w/w hexahydrocurcuminoids and 5%-10% w/w octahydrocurcuminoids to bring about inhibition in adipogenesis.

Other features and advantages of the present invention will become apparent from the following more detailed description, which illustrate, by way of example, the principle of the invention.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 2 is a graphical representation showing the reduction in body weight of test animals administered with a composition comprising tetrahydrocurcuminoids hexahydrocurcuminoids and octahydrocurcuminoids. **, P<0.01

DETAILED DESCRIPTION OF PREFERRED EMBODIMENTS

Figure 1:
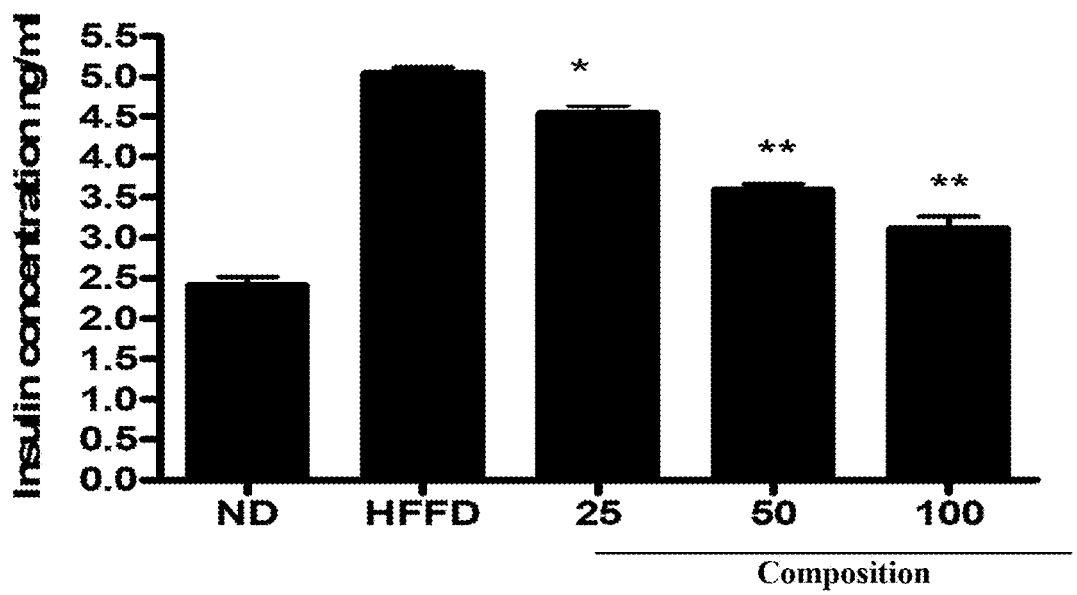
FIG. 1 is a graphical representation showing the reduction in serum insulin test animals administered with a composition comprising tetrahydrocurcuminoids hexahydrocurcuminoids and octahydrocurcuminoids. **, P<0.01

In a most preferred embodiment, the invention discloses a method for the therapeutic management of metabolic syndrome in mammals, said method comprising step of administering an effective dose, based on the body weight of said mammal, a composition comprising 70%-80% why tetrahydrocurcuminoids, 10%-20% w/w hexahydrocurcuminoids and 5%-10% w/w octahydrocurcuminoids to mammals in need of such therapeutic management. In a related aspect, the tetrahydrocurcuminoids comprise of tetrahydrocurcumin, tetrahydro-demethoxycurcumin and tetrahydro bis-demethoxycurcumin. In another related aspect, the hexahydrocurcuminoids further comprise of hexahydrocurcumin, hexahydro-demethoxycurcumin and hexahydro bis-demethoxycurcumin. In yet another preferred embodiment, octahydrocurcuminoids further comprise of octahydrocurcumin, octahydro-demethoxycurcumin and octahydrobis-demethoxycurcumin. In yet another related aspect, the therapeutic effect of managing metabolic syndrome is brough about by normalising elevated lipids levels, normalising elevated liver enzymes, reducing elevated glucose levels and inhibiting adipogenesis. In a related embodiment, the metabolic syndrome is induced by high fat fructose diet. In another related embodiment, the effective dose of the composition is 25-50 mg/kg body weight. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another preferred embodiment, the invention discloses the use of a composition comprising 70%-80% w/w tetrahydrocurcuminoids, 10%-20% w/w hexahydrocurcuminoids and 5%-10% w/w octahydrocurcuminoids in the therapeutic management of metabolic syndrome in mammals. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In yet another related aspect, the therapeutic effect of managing metabolic syndrome is brough about by normalising elevated lipids levels, normalising elevated liver enzymes, reducing elevated glucose levels and inhibiting adipogenesis. In a related embodiment, the metabolic syndrome is induced by high fat fructose diet. In another related embodiment, the effective dose of the composition is 25-50 mg/kg body weight. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another most preferred embodiment, the invention discloses a method for the therapeutic management of hyperlipidemia in mammals, said method comprising step of administering an effective dose, based on the body weight of said mammal, a composition comprising 70%-80% w/w tetrahydrocurcuminoids, 10%-20% hexahydrocurcuminoids and 5%-10% w/w octahydrocurcuminoids to mammals in need of such therapeutic management to bring about an effect of reducing the levels of a) total cholesterol, b) LDL and c) triglycerides and increasing the levels of HDL in said mammals. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In a related embodiment, hyperlipidemia is associated with high fat fructose diet induced metabolic syndrome. In another related embodiment, the effective dose of the composition is 25-50 mg/kg body weight. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In a preferred embodiment, the invention discloses a method for the therapeutic management of diabetes and associated hyperglycemia in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcutnin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In a related embodiment, diabetes and hyperglycemia are associated with high fat fructose diet induced metabolic syndrome. In another related aspect, the therapeutic effect of managing diabetes is brought about by decreasing elevated levels of glucose and insulin. In another related embodiment, the effective dose of the composition is 25-50 mg/kg body weight. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another embodiment, the invention discloses a method for the therapeutic management of liver dysfunction in mammals, said method comprising step of administering an effective dose, based on the body weight of said mammal, a composition comprising 70%-80% w/w tetrahydrocurcuminoids, 10%-20% w/w hexahydrocurcuminoids and 5%40% w/w octahydrocurcuminoids to mammals in need of such therapeutic management to reduce the elevated levels of liver enzymes. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In a related embodiment, liver dysfunction is associated with high fat fructose diet induced metabolic syndrome. In another related aspect, the liver enzymes are selected from the group consisting of Alanine transaminase and aspartate transminase. In another related embodiment, the effective dose of the composition is 25-50 mg/kg body weight. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another preferred embodiment, the invention discloses a method for inhibiting adipogenesis in mammalian cells, said method comprising step bringing into contact, mammalian adipocytes with a composition comprising 70%-80% w/w tetrahydrocurcuminoids, 10%-20% w/w hexahydrocurcuminoids and 5%-10% octahydrocurcuminoids to bring about inhibition in adipogenesis. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcutnin and octahydrobis-demethoxycurcumin. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In yet another related embodiment the bioavailability enhancer is selected from the group consisting of, but not limited to, piperine, quercetin, garlic extract, ginger extract, and naringin.

In another related aspect, one or more anti-oxidants and anti-inflammatory agents are selected from the group consisting of, but not limited to, vitamin A, D, E, K, C, B complex, rosmarinic acid, Alpha Lipoic Acid, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

Specific illustrative examples enunciating the most preferred embodiments are included herein below.

EXAMPLES

Example 1: Composition

The reductive metabolites of curcumin viz. tetrahydrocurcuminoids, hexahydrocurcuminoids and octahydrocurcuminoids are commonly biotransformed by the reductive enzymes and by hydrogenation (Mimura et. al., U.S. Pat. No. 5,266,344; Pan et al., Biotransformation of curcumin through reduction and glucuronidation in mice, Drug Metab Dispos, 1999, 27(1):486-494). They are also identified in nature and isolated from different plant sources (Majeed et al., Reductive Metabolites of Curcuminoids, Nutriscience Publishers LLC, 2019). Tetrahydocurcumin along with its analogues tetrahydrodemethoxycurcumin, tetrahydrobisdemethoxycurcumin has been isolated from *Zingiber* sp. and *Curcuma* sp. (Peng et al., Chemical constituents of *Zingiber officinale* (Zingeberaceae). Yunnan Zhiwu Yanjiu, 2007: 29(1):125-128). Tetrahydrodemethoxycurcumin and tetrahydrobisdemethoxycurcumin has been reported to be present in the rhizome of Thai Zeodary (*Curcuma zedoaria*) (Matsuda et al., Anti-allergic principles from Thai zedoary: structural requirements of curcuminoids for inhibition of degranulation and effect on the release of TNF-alpha and IL-4 in RBL-2H3 cells. Bioorg med hem, 2004; 12(22): 5891-5898). Tetrahydrocurcumin is also obtained by biotransformation from THC (Shimoda et al., Formation of tetrahydrocurcumin by reduction of curcumin with cultured plant cells of *Marchantia* polymmrpha, Nat Prod Commun, 2012, 7(4):529-530).

Hexahydrocurcuminoids is also a naturally occurring plant metabolite found in the roots and rhizomes of *Curcuma, Zingiber* and *Alpina*. Hexahydrocurcuminoids have been isolated from rhizomes of fresh ginger (Peng et al., Cytotoxic, cytoprotective and antioxidant effects of isolated phenolic compounds from fresh ginger, Fitoterapia, 2012, 83(3):568-585). Hexahydrocurcuminoids are reported to occur in either of the two enatiomeric forms (S&R) and also as a racemic mixture (Majeed et al., Reductive Metabolites of Curcuminoids, Nutriscience Publishers LLC, 2019).

Similarly, Octahydrocurcuminoids are also isolated from the rhizomes of *C. xanthorrhiza* (Uehara et al. Diarylheptanoids from the rhizomes of *Curcuma xanthorrhiza* and *Alpinia officinarum*, Chem Pharm Bull, 1987, 35(8):3298-3304). Octahydrocurcumin is also prepared by hydrogenation form tetrahydrocurcumin, in-vivo and microbial biotransformation (Majeed et al., Reductive Metabolites of Curcuminoids, Nutriscience Publishers LLC, 2019)

The composition claimed in the present invention was formulated using the following hydrogenation process:

Curcuminoids are reduced in solvent acetone under hydrogen pressure in the presence of Palladium/carbon at room temperature till the absence disappearance of the starting material. The product is isolated at off-white powder comprising Tetrahydrocurcumin, Tetrahydro demethoxycurcumin and Tetrahydro bisdemethoxycurcumin. Further, the tetrahydrocurcuminoids are reduced selectively to Hexahydrocurcuminoids in solvent ethanol under specific temperature and hydrogen pressure in the presence of Palladium/carbon till the absence disappearance of the starting material. The product is isolated as off-white powder comprising Hexahydrocurcuminoids and <5% of Octahydrocurcuminoids. For the preparation of octahydrocurcuminokls, Tetrahydrocurcuminoids are reduced to Octahydrocurcuminoids in solvent ethanol under high temperature and hydrogen pressure in the presence of Palladium/carbon till the complete conversion of the starting material. The product is isolated as off-white powder as essentially Octahydrocurcuminoids with traces of Hexahydrocurcuminoids.

The Tetrahydrocurcuminoids, Hexahydrocurcuminoids and Octahydrocurcuminoids are blended in the following proportion:

TABLE 1

Composition

| Content | Percentage (w/w) |
|---|---|
| Tetrahydrocurcuminoids | 70-80 |
| Hexahydrocurcuminoids | 10-20 |
| Octahydrocurcuminoids | 5-10 |

The composition is also available commercially as C3 Reduct® Special from Sami Labs Limited.

Example 2: Therapeutic Potential of the Composition Comprising Tetrahydrocurcuminoids, Hexahydrocurcuminoids and Octahydrocurcuminoids The therapeutic potential of the composition comprising Tetrahydrocurcuminoids, Hexahydrocurcuminoids and Octahydrocurcuminoids was tested by evaluating its ORAC and ROS & DPPH scavenging potential compared to curcuminoids, tetrahydrocurcuminoids, hexahydrocurcuminoids and octahydrocurcuminoids per se.

Oxygen Radical Absorption Capacity Assay (ORAC):

Different concentrations of the standard (Trolox) (T5 to T1) or Test samples (S3 to S1), APPH (2,2'-Azobis (2-amidinopropane dihydrochloride) and Disodium fluorescein dye were added to a 96 well dark plate. Fluorescence reading was recorded after every 1 minute for 35 minutes at 485/520 nm (Fluostar Optima Microplate Reader) (f1 . . . f35). The area under the curve (AUC) was calculated as, $$AUC=(1+f1/f0+f2/f0+ \ldots +f35/f0)$$

The net AUC was obtained by subtracting the AUC of the blank from that of the sample. The final ORAC values were expressed as micromoles of Trolox equivalents per liter or per gram of sample ($\mu$mol TE/g or $\mu$mol TE/L).

DPPH (2,2-diphenyl-1-picryl-hydrazyl-hydrate) Free Radical Assay

The test sample was dissolved in DMSO and diluted in 50% methanol for the assay. Different concentrations of pterosti¬lbene were mixed with DPPH solution in methanol in a 96 well plate. The plate was incubated in the dark for 15 min, and the absorbance was measured at 540 nm using a microplate reader (TECAN Ltd, Mannedorf, Switzerland). Blanks (DMSO, methanol) and standard (Trolox solution in DMSO) were recorded simultaneously.

The free radical scavenging activity was calculated as follows, $$\% \text{ scavenging activity}=(B-C)-(S-C)/(B-C)*100$$

Where, B is the Absorbance of reference solution, C is the Absorbance of reference solution blank (Methanol only), S is the Absorbance of the test solution and C is the Absorbance of test solution blank. The sample was screened with variable concentrations to establish the inhibition concentration (IC50, the concentration reducing DPPH absorbance by 50%). The results are tabulated as table 2:

TABLE 2

ORAC and DPPH scavenging potential of the composition comprising tetrahydrocurcuminoids, hexahydrocurcuminoids and octahydrocurcumioids (THO Composition)

| Compound | ORAC value $\mu$mole Trolox/g | DPPH-$IC_{50}$ $\mu$g/ml |
|---|---|---|
| Curcuminoids | 10115.92 ± 733.3 | 3.34 |
| Tetrahydrocurcuminoids | 11259.21 ± 642.73 | 7.7 |
| Hexahydrocurcuminoids | 11418.45 ± 626.7 | 2.24 |
| Octahydrocurcuminoids | 11335.98 ± 978.13 | 2.71 |
| THO Composition | 12114.5 ± 797.1 | 2.46 |

The results revealed that the composition comprising tetrahydrocurcuminoids, hexahydrocurcuminoids and octahydrocurcuminoids showed better ORAC and DPPH scavenging compared to curcuminoids and individual actives of the composition, indicating higher therapeutic efficacy of the composition. Further therapeutic activities were evaluated for the composition.

Example 3: In Vivo Study for Metabolic Syndrome Disease

The protocol followed for animal experiments was approved by the institutional animal ethics committee as per the Committee for the Purpose of Control and Supervision of Experiments on Animals (CPCSEA), India in compliance with Government of India guidelines and conform to the Guide for the Care and Use of Laboratory Animals published by the National Institutes of Health (NIH Publication, 8th Edition, 2011). A total of 40 C57/BL6 mice (aged 6-8 weeks) were randomly divided into five groups (mean body weight 20-22 g) of eight mice each. Animals were housed under standard laboratory conditions (temperature 23.5° C., humidity=58-64%), with 12 h light and 12 h dark cycle.

Normal Diet (10 Kcal) fed animals served as control. Metabolic syndrome was induced by High Fat Fructose Diet (HFFD) containing (60 Kcal containing 10% fructose and 50% fat diet) for 12 weeks. Different doses of test sample were administered orally to groups of mice along with HFFD. At the end of the experimental period, the animals were humanely sacrificed, organs, tissues, and blood were collected for further analysis. Bodyweight and organ weight were recorded for all animals.

Methodology

Lipid Profile

Blood TC cholesterol levels were determined by Trinder CHOD/POD End Point method under the principle of enzymatic determination of TC using the following reactions: Cholesterol ester is converted into cholesterol and fatty acids in the presence of cholesterol esterase. Cholesterol is oxidized in the presence of cholesterol oxidase to produce hydrogen peroxide. Hydrogen peroxide reacts with Phenol and 4-Aminoantipyrin in the presence of peroxidases to give Quinone and water molecule to produce red colour. The optical density is read at 500 nm against blank.

TGL were determined by GPO/POD method. TGL are hydrolyzed by lipase to glycerol and free fatty acids. Glycerol is phosphorylated by ATP in the presence of glycerol kinase to Glycerol-3-phosphate which is oxidized by the enzyme Glycerol-3-phosphate oxidase producing hydrogen peroxide. Hydrogen peroxide so formed reacts with 4-Aminoantipyrne and 4-Chlorophenol in the presence of enzyme peroxidases to produce red Quinoneimine. The intensity of color developed is proportional to the TGL concentration.

HDL and LDL parameter were measured with Direct Reagent Kit (Beacon).

Liver parameters: The enzyme levels alanine aminotransferase (ALT), aspartate aminotransferase (AST), creatinine phosphatase were determined by standard kinetic methods. The catalytic activity of an enzyme is measured by determination of the conversion rate of catalyzed chemical reaction using a specific measurement procedure. It is expressed as the amount of substance converted per unit time, in international units (IU). The catalytic concentration is the catalytic activity contained in a volume of sample and is expressed in U/L.

Blood Glucose level was estimated by glucose oxidase/Peroxidase (GOD/POD Method). Glucose oxidase (GOD) catalyzes the oxidation of glucose to gluconic acid. The formed hydrogen peroxide ($H_2O_2$), is detected by a chromogenic oxygen acceptor, phenol-aminophenazone in the presence of peroxidase (POD). The intensity of the color formed is proportional to the glucose concentration in the sample.

Serum insulin level: The serum or plasma samples were prepared by adding 150 L of the reagent and phosphate-buffered saline plus 0.05% Tween-20. The sample was further diluted 1:100 diluents. The samples, insulin control solutions, and calibrators were also prepared as well as sufficient micro plate wells to accommodate calibrators and samples in duplicates. Exactly 350 L of wash solution was added into each well, and the wash solution discarded and tapped firmly several times against absorbent paper to remove excess liquid. The mixtures were incubated for 2 h at room temperature with rigorous shaking at 300-1000 g. The plate was placed on the shaker for approximately 5 s to ensure mixture. The absorbance of the supernatant was measured at 450 nm within 30 min, and value of insulin was expressed in ng/mL (Clark and Hales, 1994). Insulin tolerance Test (ITT) After fasting for 6 h, blood samples were collected from the test animals. Then the animals were injected intraperitoneally with 1.2 U/kg bw of insulin suspended in normal saline*. Blood samples were collected at 30 and 60 min after insulin injection for the estimation of glucose. glucose load (2 g/Kgbw) was given prior to insulin injection to prevent hypoglycemia, as referenced by Gandhi et al., Gallic acid attenuates high-fat diet fed-streptozotocin-induced insulin resistance via partial agonism of PPARγ in experimental type 2 diabetic rats and enhances glucose uptake through translocation and activation of GLUT4 in PI3K/p-Akt signaling pathway European Journal of Pharmacol, 2014, 745: 201-216 and Matthews et al. Homeostasis model assessment: insulin resistance and β-cell function from fasting plasma glucose and insulin concentrations in man. Diabetologia 1985; 28: 412-41)

In vitro adipogenesis inhibition assay: The 3T3-L1 mouse embryo fibroblasts (American Type Culture Collection (ATCC, Rockville, Md., USA) were cultured in DMEM with 10% new born calf serum and 40 µg/mL gentamycin at 37° C. in a humidified atmosphere with 5% CO2. Cells were seeded at a density of 3*10^4 in 48 well plate and incubated to form a monalayer. Cells were induced to differentiate after two days of reaching 100% confluency by supplementing DMEM media with 10% fetal bovine serum, 0.25 µM dexamethasone, 0.5 mM methyl isobutyl xanthine, and insulin (1 µg/mL) together with or without various concentrations of sample. After 48 hrs of differentiation, the media was replaced with DMEM containing 10% fetal bovine serum, insulin (1 µg/mL) and sample on alternate days until the cells were harvested on day 6.

The lipid content in the adipocytes was determined by staining them with Oil Red O (ORO) staining (ORO). Briefly, the cells were fixed with 10% formalin for 30 min and stained with ORO working solution [0.3%] for 60 min at room temperature and visualized by an inverted phase-contrast microscope (Olympus, Tokyo, Japan,). The lipids stained with ORO were extracted from the cells using 4% triton X-100 in isopropanol and quantified at a wavelength of 520 nm.

Results

Lipid Profile

The results were tabulated in Table 3.

TABLE 3

| | Lipid Profile | | | |
|---|---|---|---|---|
| Groups | Total Cholesterol (mg/dl) | HDL (mg/dl) | TG (mg/dl) | LDL (mg/dl) |
| Normal Diet | 83.88 ± 2.75 | 64.38 ± 2.92 | 105.63 ± 2.00 | 6.73 ± 0.37 |
| HFFD control | 190.63 ± 2.62 | 24.38 ± 2.77 | 234.38 ± 2.67 | 76.45 ± 2.69 |
| Composition (25 mg/Kg) | 174.38 ± 2.92 | 33.00 ± 2.62 | 181.00 ± 3.59 | 63.44 ± 1.50 |
| Composition (50 mg/Kg) | 146.83 ± 2.32 | 43.83 ± 2.99 | 144.50 ± 2.74 | 39.57 ± 1.15 |
| Composition (100 mg/Kg) | 92.75 ± 2.63 | 58.00 ± 2.58 | 122.25 ± 4.99 | 19.15 ± 0.61 |

High fat fructose diet increased the levels of total cholesterol, triglycerides, and LDL. The composition decreased the levels of total cholesterol, triglycerides and LDL in a dose dependent manner. Similarly, the composition also increased the reduced levels of HDL in the test animals, indicating that the composition was very effective in managing hyperlipidemia in metabolic syndrome.

Liver Parameters and Glucose Levels

The levels of glucose and liver enzymes were elevated by administration of high fat fructose diet. The composition comprising tetrahydrocurcuminoids, hexahydrocurcuminoids and octahydrocurcuminoids normalized the elevated liver enzymes that were altered in metabolic syndrome and was prevented liver dysfunction (table 4). Similarly, the composition also reduced the elevated glucose and insulin levels in serum indicating the potential of the composition for use as an anti-diabetic agent (Table 4, FIG. 1)

Figure 2:
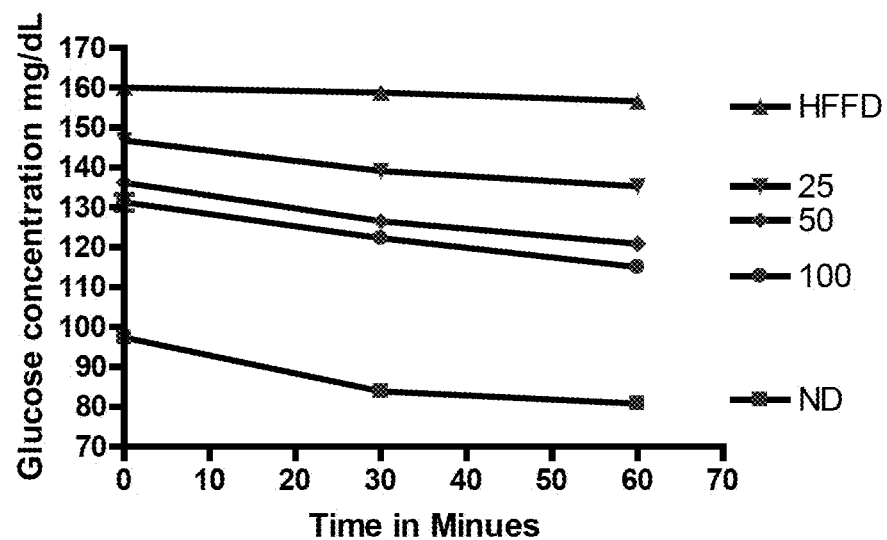
FIG. 2 is a graphical representation showing the reduction in glucose levels in test animals administered with a composition comprising tetrahydrocurcuminoids hexahydrocurcuminoids and octahydrocurcuminoids. **, P<0.01

The insulin tolerance test suggested that the ability of the animals to tolerate glucose was reduced in HFD mice (showed higher Blood Glucose Concentration). In this assay, the degree to which blood glucose concentrations fall following insulin administration represent the efficiency of whole-body insulin action. The HFD-fed mice showed an impaired reduction of blood glucose levels compared to the control animals at all time points during the ITT, thus suggesting insulin resistance. Supplementation with the composition along with HFD showed reduction in the blood glucose, suggesting that insulin resistance can be reduced by the composition (FIG. 2)

Body Weight Reduction

Figure 3:
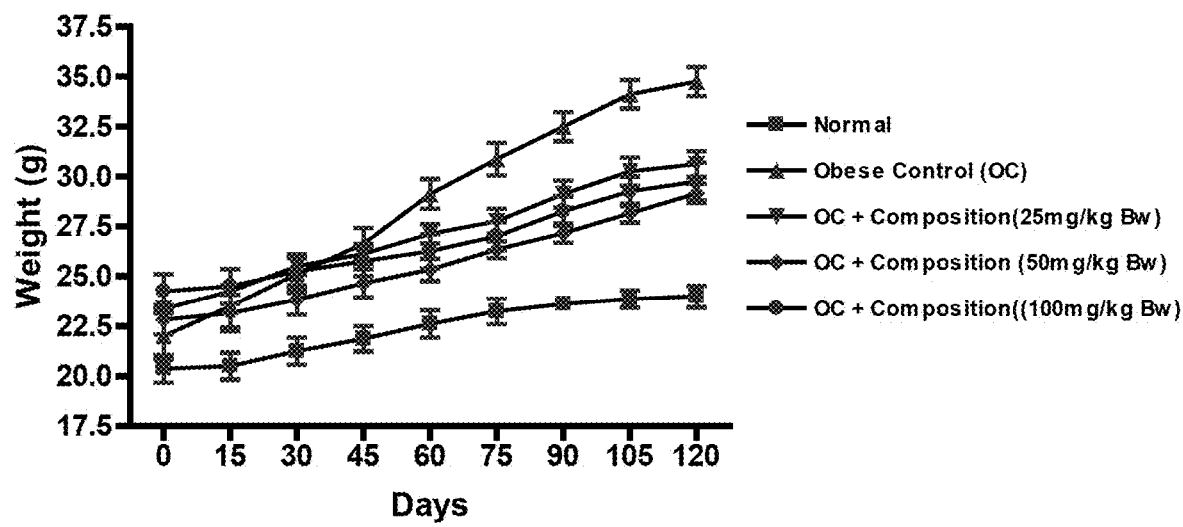

Moderate reduction in body weight was observed in animals supplemented with the composition. 11.8%, 16.1% and 14.4% reduction was seen at 25, 50 and 100 mg/kg (FIG. 3)

Inhibition of Adipogenesis

Figure 4:
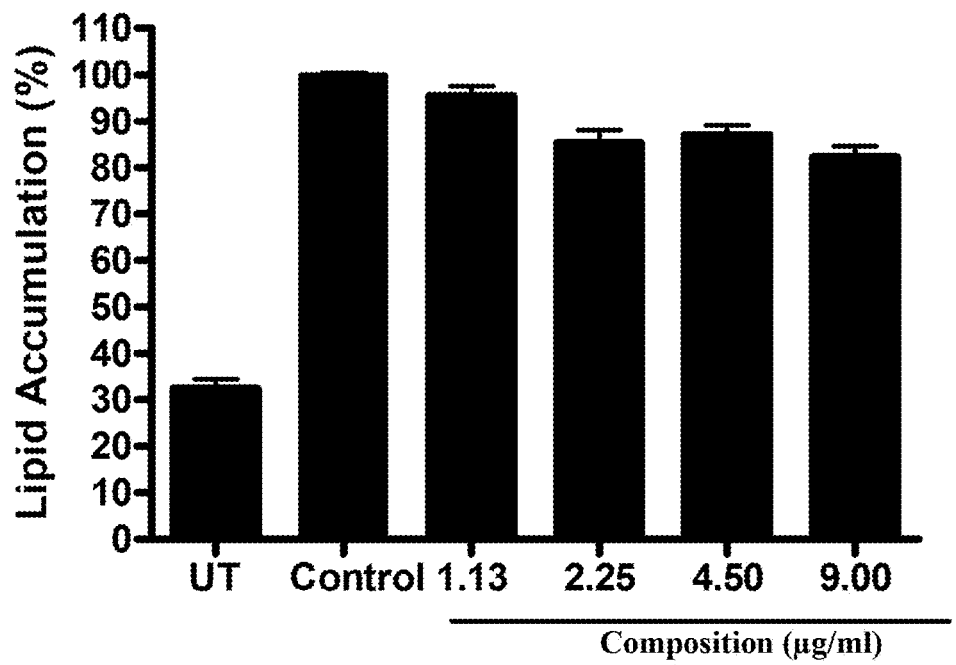
FIG. 4 is a graphical representation showing the reduction in lipid accumulation in 3T3 cells incubated with a composition comprising tetrahydrocurcuminoids hexahydrocurcuminoids and octahydrocurcuminoids.
Figure 5:
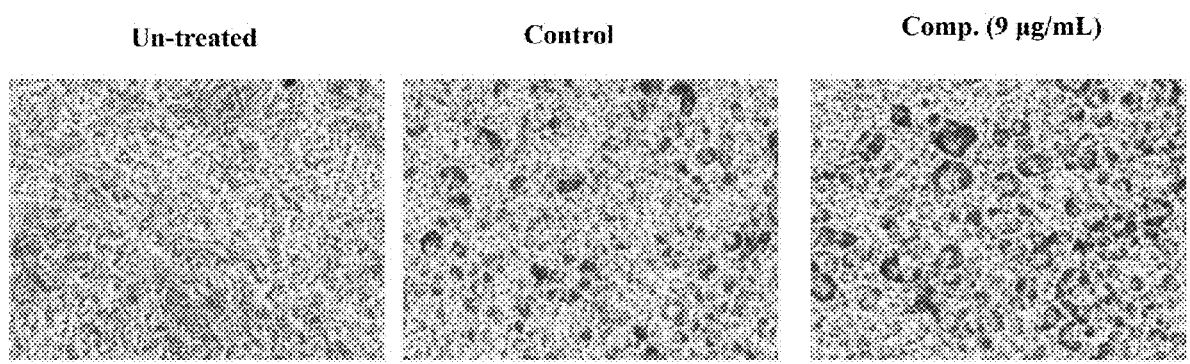
FIG. 5 is a Oil Red O (ORO) staining of mouse 3T3 cells showing the inhibiting of adipogenesis by the composition comprising tetrahydrocurcuminoids hexahydrocurcuminoids and octahydrocurcuminoids.

The composition comprising tetrahydrocurcuminoids, hexahydrocurcuminoids and octahydrocurcuminoids was tested for its potential in inhibiting adipogenesis. The results indicated that the composition was effective in reducing adipogenesis in 3T3 preadipocytes, (FIG. 4 and FIG. 5) indicating the potential of the composition for use as an anti-obesity agent.

Overall, the composition comprising tetrahydrocurcuminoids, hexahydrocurcuminoids and octahydrocurcuminoids was effective in managing metabolic syndrome by normalizing lipid levels, glucose and insulin levels in blood, reducing the elevated liver enzymes and inhibiting adipogenesis. The composition is very suitable for use as a supplement for the management of diet induced metabolic syndrome.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method for the therapeutic management of metabolic syndrome in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management.

2. The method as in claim 1, wherein the tetrahydrocurcuminoids comprise of tetrahydrocurcumin, tetrahydrodemethoxycurcumin and tetrahydrobis-demethoxycurcumin.

3. The method as in claim 1, wherein the hexahydrocurcuminoids comprise of hexahydrocurcumin, hexahydrodemethoxycurcumin and hexahydrobis-demethoxycurcumin.

4. The method as in claim 1, wherein the octahydrocurcuminoids further comprise of octahydrocurcumin, octahydro-demethoxycurcumin and octahydrobis-demethoxycurcumin.

5. The method as in claim 1, wherein the therapeutic effect is normalising elevated lipids levels, normalising elevated liver enzymes, reducing elevated glucose levels and inhibiting adipogenesis.

6. The method as in claim 1, wherein the metabolic syndrome is induced by high fat fructose diet.

7. The method as in claim 1, wherein the effective dose of the composition is 25-50 mg/kg body weight.

8. The method as in claim 1, wherein the composition further comprises of stabilizing agents, bioavailability enhancers and antioxidants, pharmaceutically or nutraceutically or cosmeceutically accepted excipients and enhancers.

9. The method as in claim 1, wherein the mammal is human.

10. A method for the therapeutic management of hyperlipidemia in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management to bring about an effect of reducing the levels of a) total cholesterol, b) LDL and c) triglycerides and increasing the levels of HDL in said mammals.

11. The method as in claim 10, wherein the tetrahydrocurcuminoids comprise of tetrahydrocurcumin, tetrahydrodemethoxycurcumin and tetrahydrobis-demethoxycurcumin.

12. The method as in claim 10, wherein the hexahydrocurcuminoids comprise of hexahydrocurcumin, hexahydrodemethoxycurcumin and hexahydrobis-demethoxycurcumin.

13. The method as in claim 10, wherein octahydrocurcuminoids further comprise of octahydrocurcumin, octahydro-demethoxycurcumin and octahydrobis-demethoxycurcumin.

14. The method as in claim 10, wherein hyperlipidemia is associated with high fat fructose diet induced metabolic syndrome.

15. A method for the therapeutic management of diabetes and associated hyperglycemia in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management.

16. The method as in claim 15, wherein the tetrahydrocurcuminoids comprise of tetrahydrocurcumin, tetrahydrodemethoxycurcumin and tetrahydrobis-demethoxycurcumin.

17. The method as in claim 15, wherein the hexahydrocurcuminoids comprise of hexahydrocurcumin, hexahydrodemethoxycurcumin and hexahydrobis-demethoxycurcumin.

18. The method as in claim 15, wherein the octahydrocurcuminoids further comprise of octahydrocurcumin, octahydro-demethoxycurcumin and octahydrobis-demethoxycurcumin.

19. The method as in claim 15, wherein diabetes and hyperglycemia are associated with high fat fructose diet induced metabolic syndrome.

20. A method for the therapeutic management of liver dysfunction in mammals, said method comprising step of administering an effective dose, based on the body weight of said mammal, a composition comprising 70%-80% w/w tetrahydrocurcuminoids, 10%-20% w/w hexahydrocurcuminoids and 5%-10% w/w octahydrocurcuminoids to mammals in need of such therapeutic management to reduce the elevated levels of liver enzymes.

21. The method as in claim 20, wherein the tetrahydrocurcuminoids comprise of tetrahydrocurcumin, tetrahydrodemethoxycurcumin and tetrahydrobis-demethoxycurcumin.

22. The method as in claim 20, wherein the hexahydrocurcuminoids comprise of hexahydrocurcumin, hexahydrodemethoxycurcumin and hexahydrobis-demethoxycurcumin.

23. The method as in claim 20, wherein the octahydrocurcuminoids further comprise of octahydrocurcumin, octahydro-demethoxycurcumin and octahydrobis-demethoxycurcumin.

24. The method as in claim 20, wherein the liver dysfunction is associated with high fat fructose diet induced metabolic syndrome.

25. The method as in claim 20, wherein the liver enzymes are selected from the group consisting of Alanine transaminase and aspartate transminase.

26. A method for inhibiting adipogenesis and reducing body weight in an obese mammal, said method comprising step of administering a composition comprising 70%-80% w/w tetrahydrocurcuminoids, 10%-20% w/w hexahydrocurcuminoids and 5%-10% w/w octahydrocurcuminoids to said mammal, to bring about inhibition in adipogenesis and reduction in body weight.

27. The method as in claim 26, wherein the tetrahydrocurcuminoids comprise of tetrahydrocurcumin, tetrahydrodemethoxycurcumin and tetrahydrobis-demethoxycurcumin.

28. The method as in claim 26, wherein the hexahydrocurcuminoids comprise of hexahydrocurcumin, hexahydrodemethoxycurcumin and hexahydrobis-demethoxycurcumin.

29. The method as in claim 26, wherein the octahydrocurcuminoids comprise of octahydrocurcumin, octahydrodemethoxycurcumin and octahydrobis-demethoxycurcumin.

30. The method as in claim 26, wherein the mammal is human.

* * * * *